United States Patent [19]
Watkins, III et al.

[11] Patent Number: 5,820,555
[45] Date of Patent: Oct. 13, 1998

[54] METHOD FOR SELECTIVELY CREATING AND ALTERING THE SHAPE OF A BODY CAVITY

[76] Inventors: Frank T. Watkins, III, 570 Oak Knoll La., Menlo Park, Calif. 94025; Richard L. Mueller, Jr., 2305 Cypress Point, Byron, Calif. 94514; Tim J. Kovac, 33 Ashler Ave., Los Gatos, Calif. 95030; Diane E. Caramore, 1235 Jefferson Ave., Apt. 200, Redwood City, Calif. 94062

[21] Appl. No.: 774,995

[22] Filed: Dec. 27, 1996

Related U.S. Application Data

[63] Continuation of Ser. No. 339,068, Nov. 14, 1994, abandoned, which is a continuation-in-part of Ser. No. 62,707, May 18, 1993, Pat. No. 5,520,609, which is a continuation of Ser. No. 706,781, May 29, 1991, abandoned.

[51] Int. Cl.$^6$ .................................................. A61B 17/02
[52] U.S. Cl. ........................................... 600/204; 600/228
[58] Field of Search ................................... 600/204, 215, 600/227, 228, 229, 230

[56] References Cited

U.S. PATENT DOCUMENTS

| | | | |
|---|---|---|---|
| 3,638,973 | 2/1972 | Poletti | 600/229 X |
| 4,143,652 | 3/1979 | Meier et al. | 600/229 X |
| 4,622,955 | 11/1986 | Fakhrai | 128/20 |
| 4,949,707 | 8/1990 | Le Vahn et al. | 600/228 X |
| 5,372,147 | 12/1994 | Lathrop et al. | 600/200 X |
| 5,415,159 | 5/1995 | Oritz et al. | 600/230 |
| 5,441,042 | 8/1995 | Putman | 600/227 |

FOREIGN PATENT DOCUMENTS

| | | | |
|---|---|---|---|
| 0 415 417 A1 | 6/1991 | European Pat. Off. | A61B 17/02 |
| 0 415 417 A2 | 6/1991 | European Pat. Off. | A61B 19/00 |
| 29 23 105 A1 | 11/1980 | Germany | A61B 17/34 |
| 9114392 | 10/1991 | WIPO | 600/204 |

*Primary Examiner*—Michael H. Thaler
*Attorney, Agent, or Firm*—Limbach & Limbach L.L.P.

[57] ABSTRACT

A lifting device for laparoscopic procedures is provided with joints to enable an instrument carried by the device to be rotated to selectively adjust its pitch, roll and yaw. The adjustment provides a mechanism whereby the instrument may be connected to the arm in a variety of rotational orientations and accommodate different conditions to provide operating space within the body of a patient. Various mechanisms are provided to selectively lock the joints.

4 Claims, 8 Drawing Sheets

METHOD FOR SELECTIVELY CREATING AND ALTERING THE SHAPE OF A BODY CAVITY

RELATED APPLICATIONS

This application is a continuation of application Ser. No. 08/339,068 filed Nov. 11, 1194, now abandoned, which is a continuation-in-part of application Ser. No. 08/062,707, filed May 18, 1993, now Pat. No. 5,520,609 of inventors Frederic H. Moll, Albert K. Chin, Diane E. Caramore and Frank T. Watkins, III, which in turn is a continuation of application Ser. No. 07/706,781, filed May 29, 1991, now abandoned. It also relates to Ser. No. 07/890,033, filed May 28, 1992, of inventors Frederic H. Moll, Albert K. Chin, Rick Kaufmann and Charles Gresl, Jr.

BACKGROUND OF THE INVENTION

The present invention relates to an improved tool holder for adjustably securing a laparoscopic instrument to a mechanical support arm disposed externally of a patient's body and, more particularly, is concerned with such a holder which provides for pivotal movement of the instrument relative to the arm about intersecting axes and for selective locking against such movement to hold the instrument in adjusted angular orientation relative to the arm. In its more specific aspects, the invention is concerned with such a holder which may be used with a laparoscopic lifting device to adjustably support the device at various angular orientations relative to the lifting arm.

Related application Ser. No. 08/062,707 discloses a variety of mechanical lifting devices for lifting the wall of a body cavity during laparoscopic surgery, without insufflation. Some of these devices are carried by jacks disposed externally of the patient's body. Application Ser. No. 07/890, 033 also discloses such devices and an embodiment wherein the device may pivot about a vertical axis relative to its support arm. The present invention provides an improved connection for securing the later type of device to a support arm whereby the angular position of the arm about "pitch," "roll," and "yaw" axes may be adjusted.

The prior art teaches various types of adjustable lifting devices for use with surgical retractors. One such device may be seen in German patent DE 29 23 105 wherein an angularly adjustable lifting arm is provided for a trocar sleeve insert. In the case of the arm of this device, the insert in freely pivotal relative to the arm and no means is provided to selectively lock the angular orientation of the insert relative to the arm. U.S. Pat. No. 4,622,955 discloses a jack for a surgical retractor which includes an arm adapted to be positioned over the patient's body and secured to the retractor by a crank operated lifting cable. No means is provided to selectively lock the angular orientation of the retractor relative to the arm. European patent applications 0 415 416 A1 and 0 415 417 A2 disclose surgical retractors having articulated arms with joints which may be selectively locked to adjust the position of the retractors. These arms are not designed or adapted for use with laparoscopic lifting instruments of the type which the present invention is concerned.

SUMMARY OF THE INVENTION

The inventive apparatus supports a laparoscopic lifting device disposed internally of the body of a patient on a lifting arm disposed externally of the patient's body. It provides means to secure the lifting device to the arm and a joint to adjust the roll and pitch of an instrument secured to the arm. Lock means is associated with the joint to selectively fix the instrument in adjusted position.

The method of the invention provides for lifting of the wall of a patient's body cavity with a laparoscopic lifting device disposed internally of the wall. It includes the steps of connecting the lifting device to an externally disposed lifting jack through means of a multiple axis joint. The rotational orientation of the lifting device is adjusted through the joint and, once adjusted, the joint is locked to fix the lifting device relative to at least one axis of adjustment. Then the elevation of the lifting device is adjusted through the lifting jack.

A principal object of the present invention is to provide a means for securing a laparoscopic lifting device disposed internally of a patient's body to an externally disposed lifting arm through a connection which provides for selective adjustment of the pitch and roll of the lifting device relative to the arm.

Another object of the invention is to provide such a connection which enables the lifting device to selectively enlarge and alter the shape of the body cavity.

Still another object of the invention is to provide such a connection which enables the lifting device to be secured to the arm at various angular orientations relative thereto.

Yet another object of the invention is to provide such a connection which provides freedom of angular movement of the lifting device relative to the lifting arm and may be selectively operated to lock the lifting device at fixed angular orientations relative to the arm.

A further object of the invention is to provide such a connection which can accommodate different conditions, such as distortion of the lifting device as the result of the obesity of the patient, or maneuvering of the patient into a laterally titled position by rotation of the operating table.

Yet a further object of the invention is to provide a method and apparatus whereby the wall of a body cavity may be lifted and shaped to provide space for access to select organs or portions of organs.

The foregoing and other objects of the invention will become apparent when viewed in light of the following detailed description and accompanying drawings.

DESCRIPTION OF THE PREFERRED EMBODIMENTS

Figure 1:
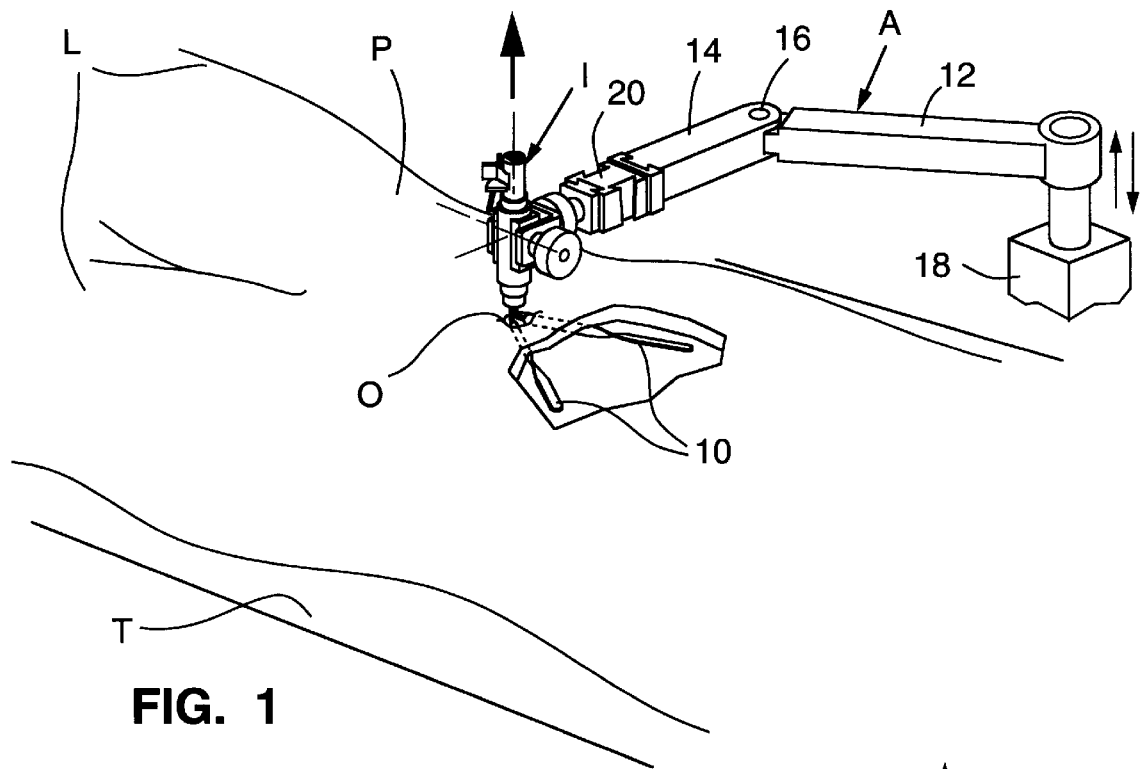
FIG. 1 is a perspective view of a patient's body on an operating table, with a laparoscopic lifting device in place within the body and secured to a lifting arm through means of a first embodiment of the present invention; a portion of the abdominal wall being broken away for purposes of illustration.
Figure 2:
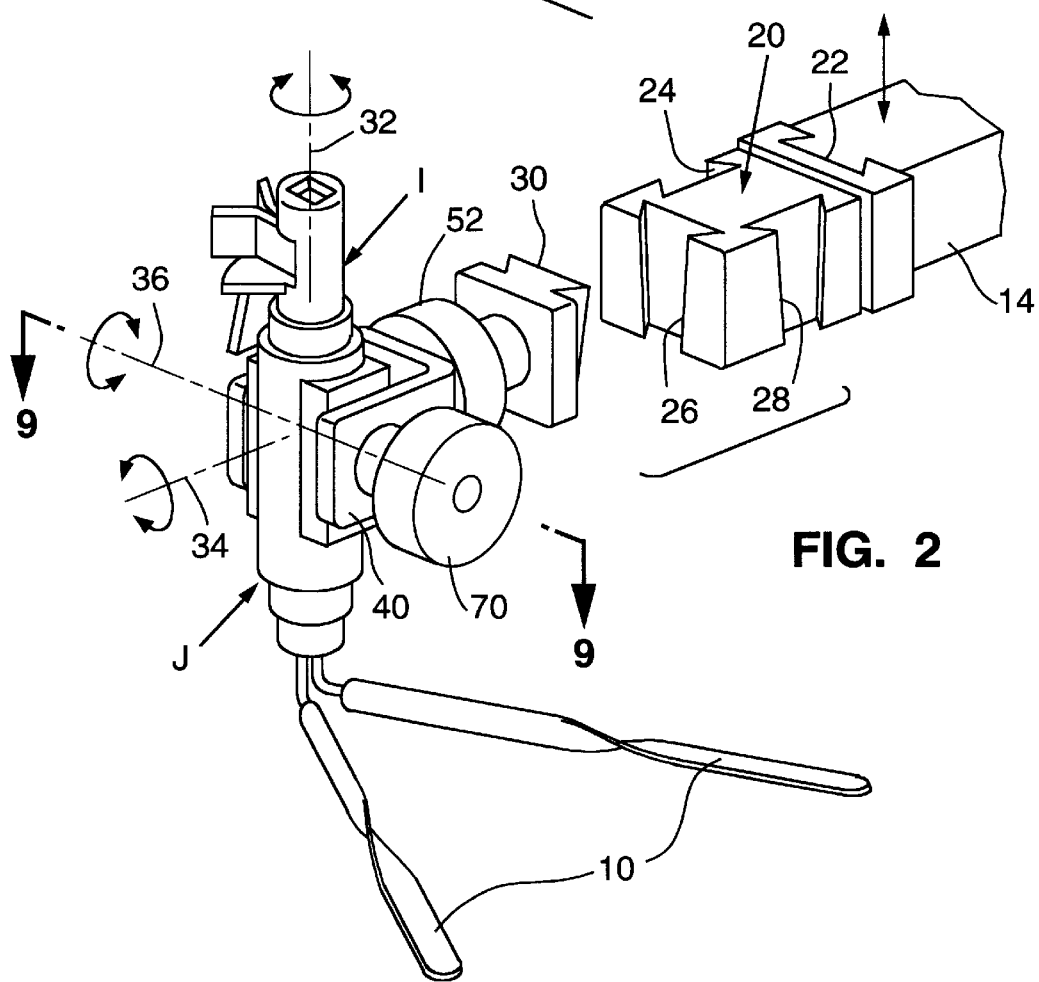
FIG. 2 is a enlarged view of the FIG. 1 first embodiment connection, shown with the lifting arm and lifting device in exploded perspective, illustrating the axes of pitch, roll and yaw movement.

FIG. 1 illustrates the torso of a patient "P" supported on an operating table "T" during the course of laparoscopic surgery. The legs of the patient, designated "L" extend to the left, as shown in this figure. A small laparoscopic opening "O" is formed in the abdominal wall of the patient and a laparoscopic lifting instrument "I" is shown extending through this opening. The instrument "I" may be of the type shown in application Ser. No. 07/890,093. Although the abdominal wall is shown broken-away in FIG. 1 in order that the lifting arms 10 of the instrument may be seen, it should be understood that the opening shown is for illustrative purposes only and that no such opening is formed during laparoscopic surgery.

The instrument "I" is supported on a mechanical lifting arm "A" disposed externally of the patient's body. The arm "A" has articulated sections 12 and 14 joined by an elbow-like joint 16 which provides a vertical hinge, while enabling lifting force to be transmitted from the section 12 to the section 14. The section 12 is supported on a jack 18 mounted either to the operating room table "T", or a separate support stand. The jack 18 may be powered up and down, as shown by the arrow lines in FIG. 1, to raise and lower the arm "A." A mounting block 20 is secured to the distal end of the section 14 for purposes of attaching the lifting arm "A" to the instrument "I." The block 20 is formed with a first tapered dovetail slot 22 engagable with a dovetail formed on the distal end of the arm section 14. Tapered dovetail slots 24, 26 and 28 spaced 90° C. from one another are formed in the sides of the block 20 for select engagement by a tapered dovetail 30 mounted to the instrument "I."

While the instrument "I" has an internal structure and mode of operation corresponding to that of application Ser. No. 07/890,033 and is mounted for rotational movement about a vertical "yaw" axis 32, it is also mounted for select rotational movement about a "pitch" axis 34 and a "roll" axis 36. Adjustment about the latter axes is provided through means of the connection of the present invention.

Figure 9:
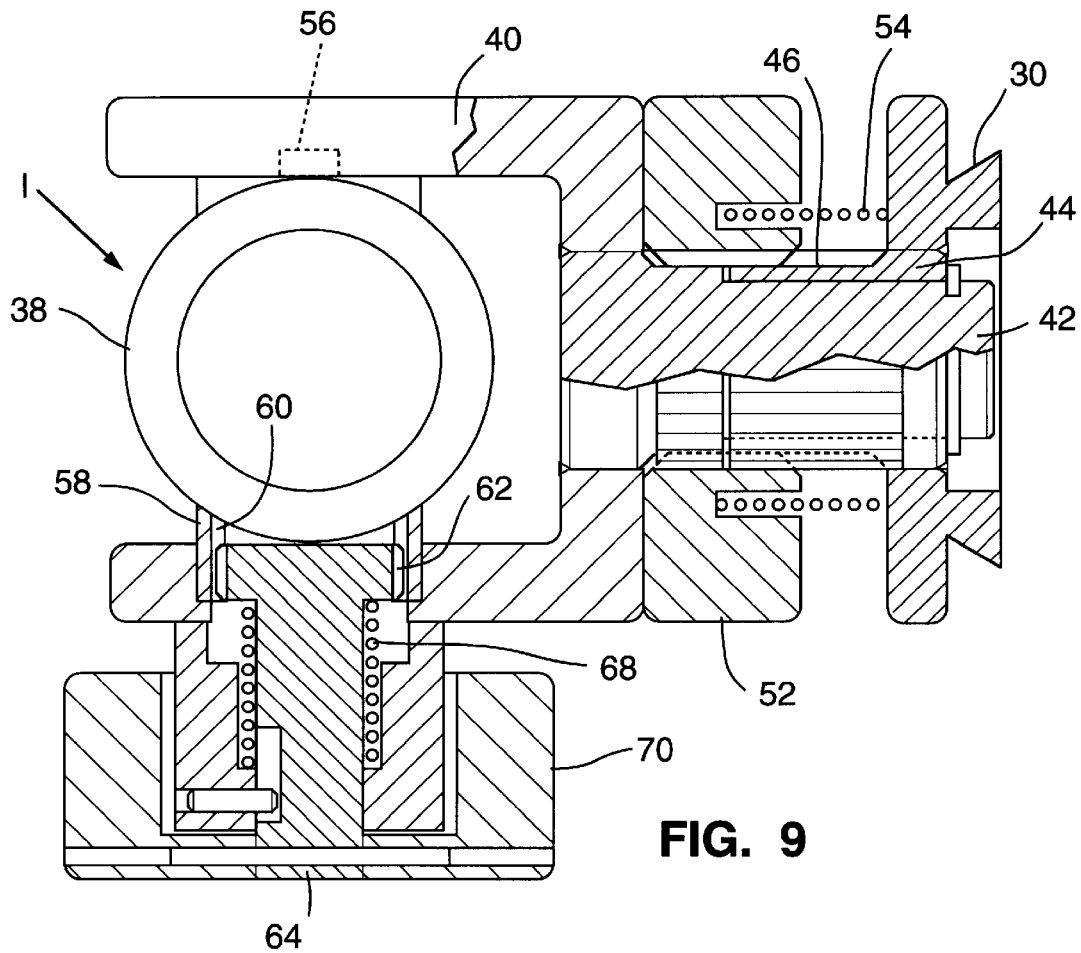
FIG. 9 is a cross-sectional view of the connection taken on the plane designated by line 9—9 of FIG. 2, illustrating the connection in the condition locked against pitch and roll movement.
Figure 10:
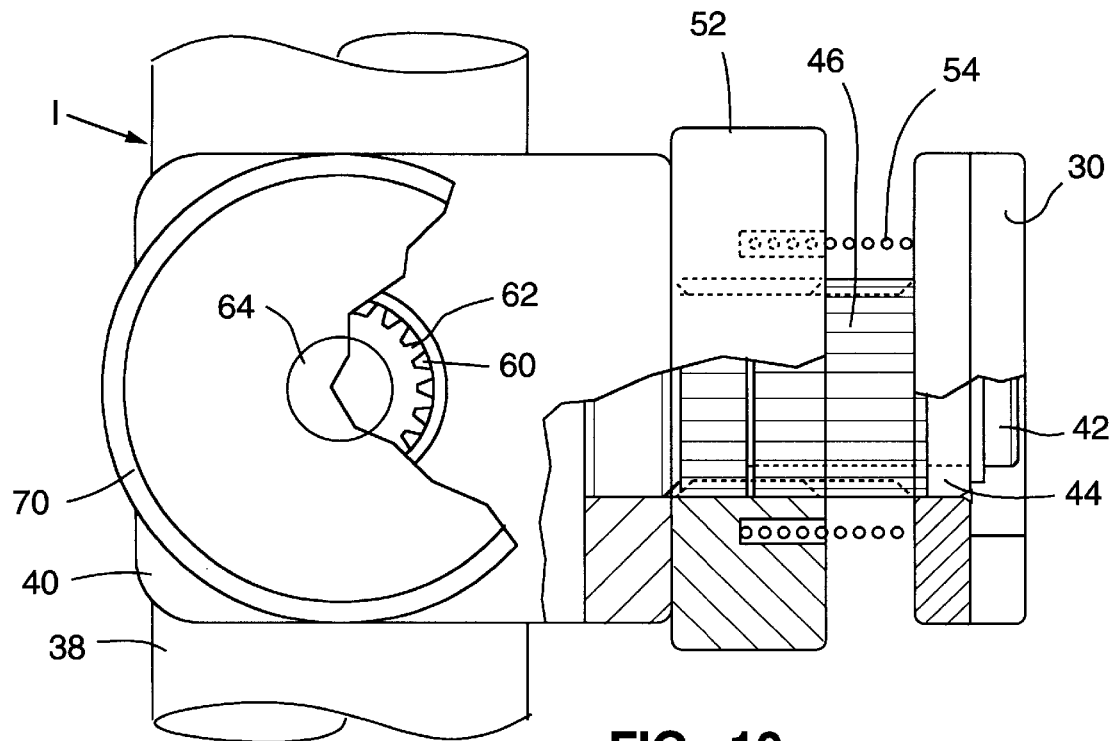
FIG. 10 is an elevational view of the connection shown in FIG. 9, viewed from the bottom at 90° C. relative to the section of FIG. 9, with parts thereof broken away for purposes of illustration.
Figure 11:
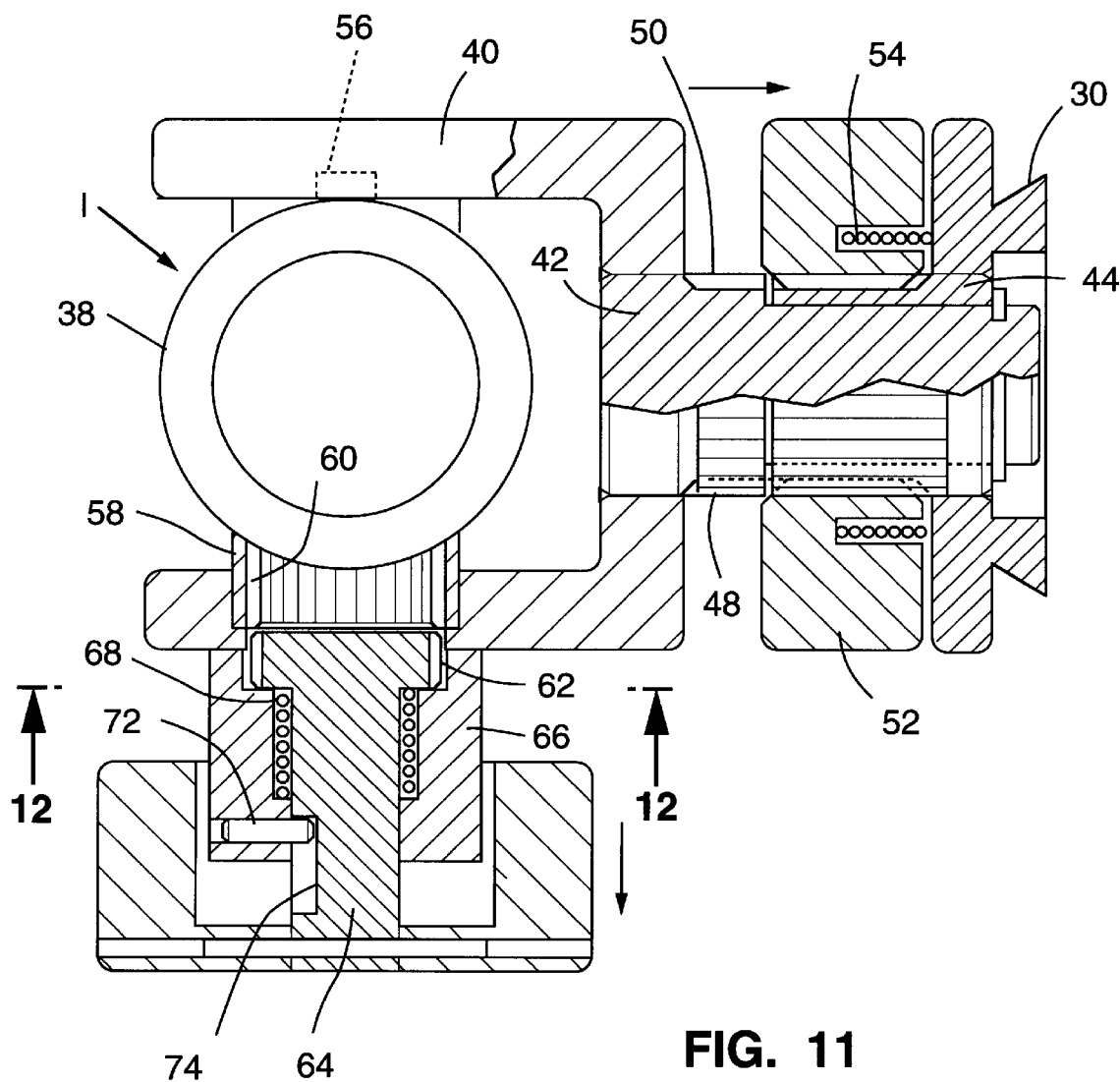
FIG. 11 is a cross-sectional view corresponding to that of FIG. 9, illustrating the connection in the condition released for pitch and roll movement.
Figure 12:
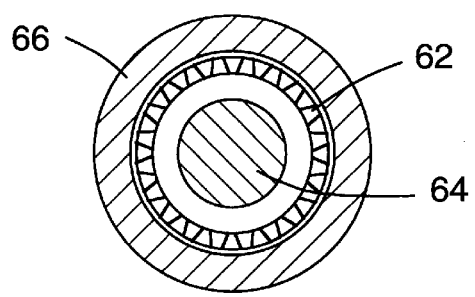
FIG. 12 is a cross-sectional view taken on the plane designated by line 12—12 of FIG. 11.

The construction of the joint shown in FIG. 1, designated in its entirety by the letter "J" may best be seen from FIGS. 9–12. As there shown, it will be seen that the outer housing 38 of the instrument "I" is mounted in a fork structure 40. The fork structure 40 is mounted for rotation about the pitch axis 34 by a shaft 42 fixed to the fork structure and journaled within a bearing sleeve 44 fixed to the dovetail 30. The outer surface of the sleeve 44 is formed with a longitudinally extending spline 46. The shaft 42 is formed with a collar 48 having a longitudinally extending spline 50 complemental to the spline 46. An internally splined collar 52 mates with and is slidably received on the splines 46 and 50 for movement between a position locking the shaft 42 and bearing sleeve 44 against relative rotational movement, as shown in FIG. 9, and a position releasing the shaft and sleeve for such relative movement, as shown in FIG. 11. A compression coil spring 54 is interposed between the back of the dovetail 30 and the slidable collar 52 to normally urge the collar to the locked condition shown in FIG. 9.

The instrument "I" is pivotally mounted in the fork structure 40 for movement about the roll axis 36 by a pin 56 journaled in one side of the fork structure and a sleeve 58 journaled in the other side of the fork structure. The pin 56 and sleeve 58 are longitudinally aligned and fixed relative to the housing 38 of the instrument "I."

The sleeve 58 is provided with a longitudinally extending internal spline 60. Select locking of the sleeve 58 and attached instrument "I" is provided by engaging the spline 60 with the splined head 62 of a locking bolt 64 slidably carried by the fork structure 40. The bolt 64 is received within a collar 66 fixed to the fork structure 40. A compression coil spring 68 normally biases the splined head 62 into engagement with the spine 60 of the sleeve 58. Select retraction of the bolt to the disengaged position is provided by an enlarged manually grippable knob 70 secured to the bolt. A key 72 carried by the collar 66 slidably engages a keyway 74 within the bolt 64 to hold the bolt against rotation relative to the collar.

A shown in FIG. 9, the splined head 62 of the bolt 64 is engaged with the spine 60 of the sleeve 58 to lock the instrument "I" against rotation about the roll axis 36. The spring 68 normally biases the head 62 into this condition. Release of the instrument for rotation about the roll axis is provided by manually withdrawing the knob 70. Such withdrawal removes the splined head 62 from engagement with the spline 60 of the sleeve 58.

Adjustment of the pitch of the lifting instrument will be useful in at least three instances, namely:

(1) Upon insertion of the dovetail 30 of the instrument "I" into the dovetail slot of the mounting block 20. Such adjustment is frequently desirable because the lifting instrument is pitched at an angle when it is first inserted into and engaged with the wall of a body cavity. The user must manually align the lifting instrument with the mounting block to engage the dovetail and dovetail slot. Provision of pitch adjustment facilitates such alignment.

(2) When operating on obese patients where the weight of the patient's excess fat may be enough to bend the arms of the lifting device.

Figure 3:
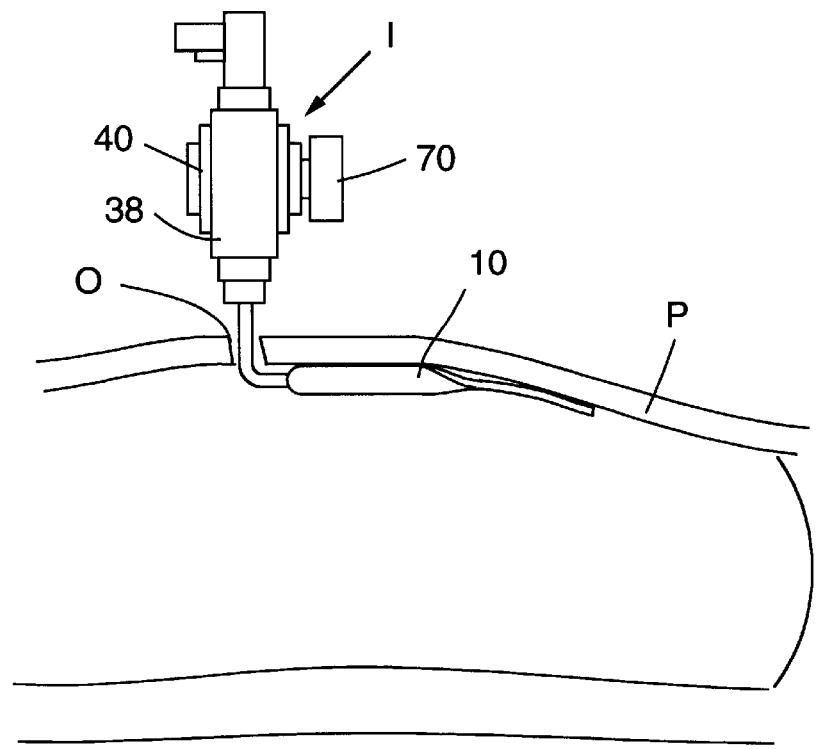
FIG. 3 is a cross-sectional elevational view showing the lifting device of FIG. 1, with the arms of the lifting device bent downwardly as the result of the patient's obesity.
Figure 4:
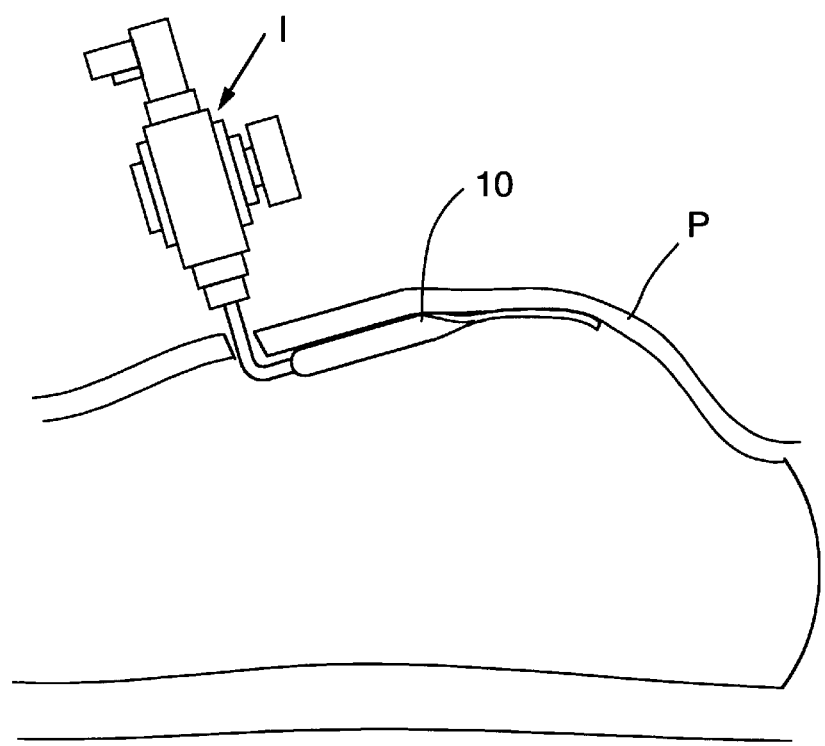
FIG. 4 is a cross-sectional elevational view similar to FIG. 1, showing the angle of the lifting device adjusted about the pitch axis to make room within the patient's body cavity, notwithstanding that the arms of the lifting device are bent due to the patient's obesity.

Such a condition is shown in FIG. 3 where the legs 10 are bent downwardly and, thus, may not provide the desired degree of exposure within the body cavity. By adjusting the pitch as shown in FIG. 4, the legs can be brought up to provide more exposure for the laparoscopic procedure.

(3) In any circumstance where it is desired to make more room within a body cavity to one side or the other of the pitch axis.

Figure 5:
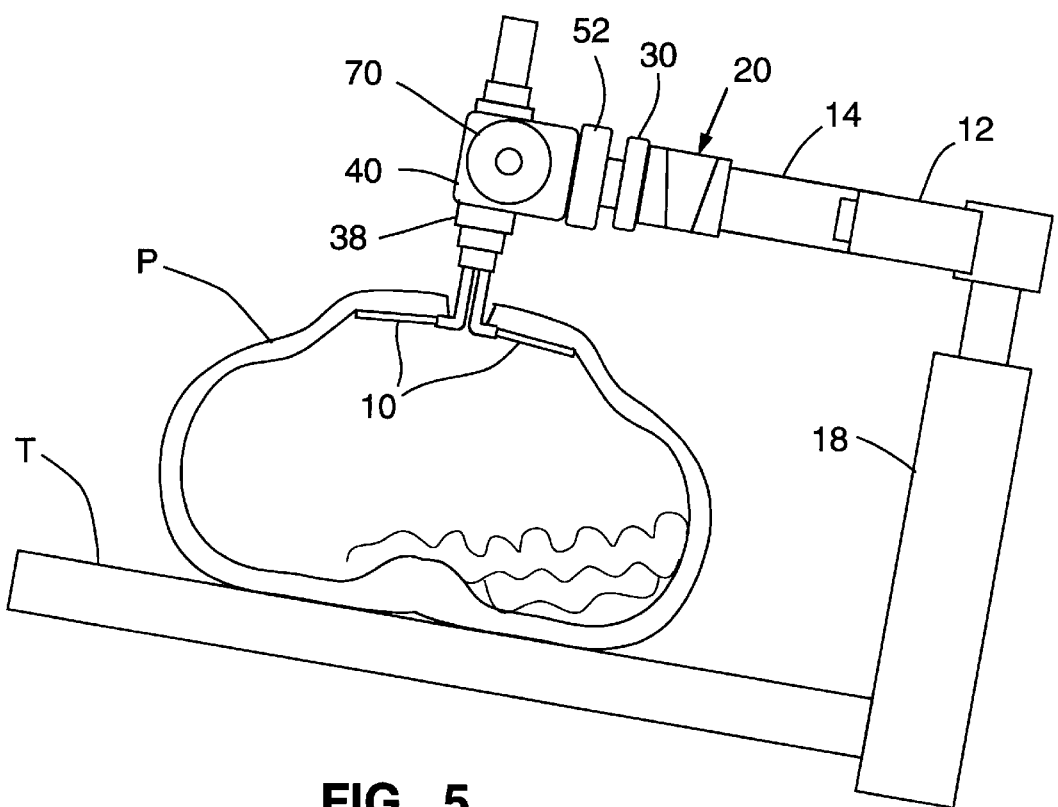
FIG. 5 is a cross-sectional elevational view showing the lifting device of FIG. 1 with the operating table rotated to maneuver the patient into a laterally tilted position and the organs within the patient's body shifted to one side as the result of gravity.
Figure 6:
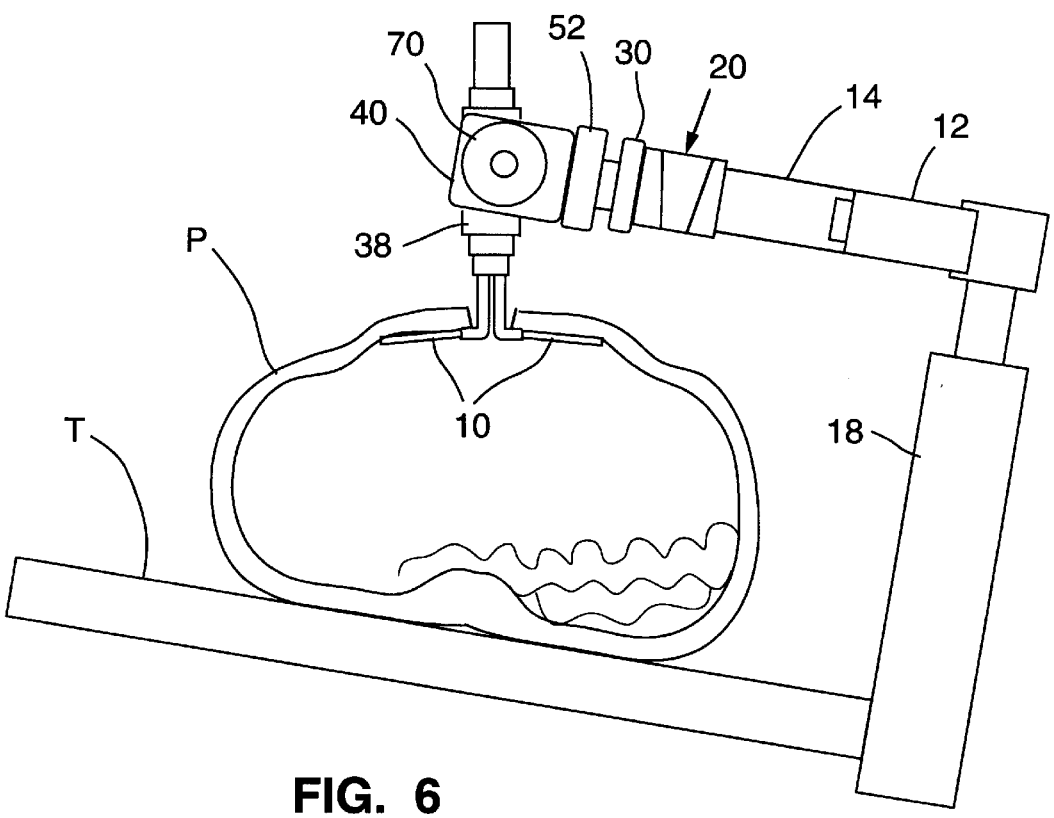
FIG. 6 is a cross-sectional elevational view corresponding to that of FIG. 5, illustrating the lifting device pivoted about the roll axis through means of the connection of the present invention to provide additional space above the organs which have shifted due to gravity.
Figure 7:
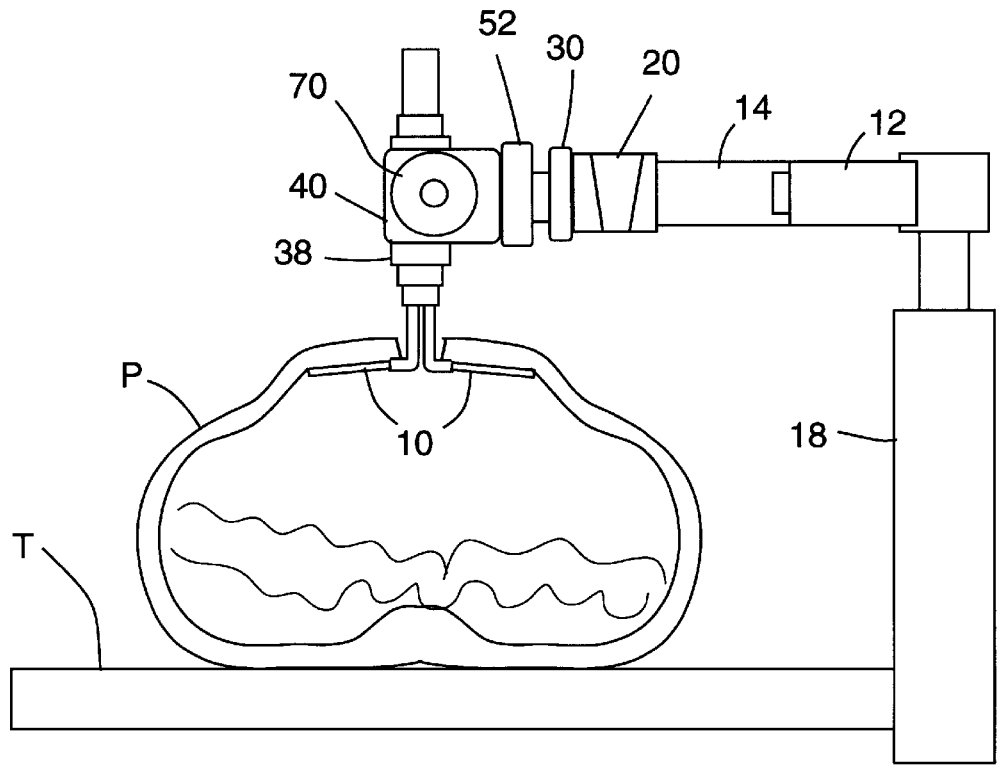
FIG. 7 is a cross-sectional elevational view showing the lifting device of FIG. 1 with the arms of the device lifting in a condition generally parallel to the operating table.
Figure 8:
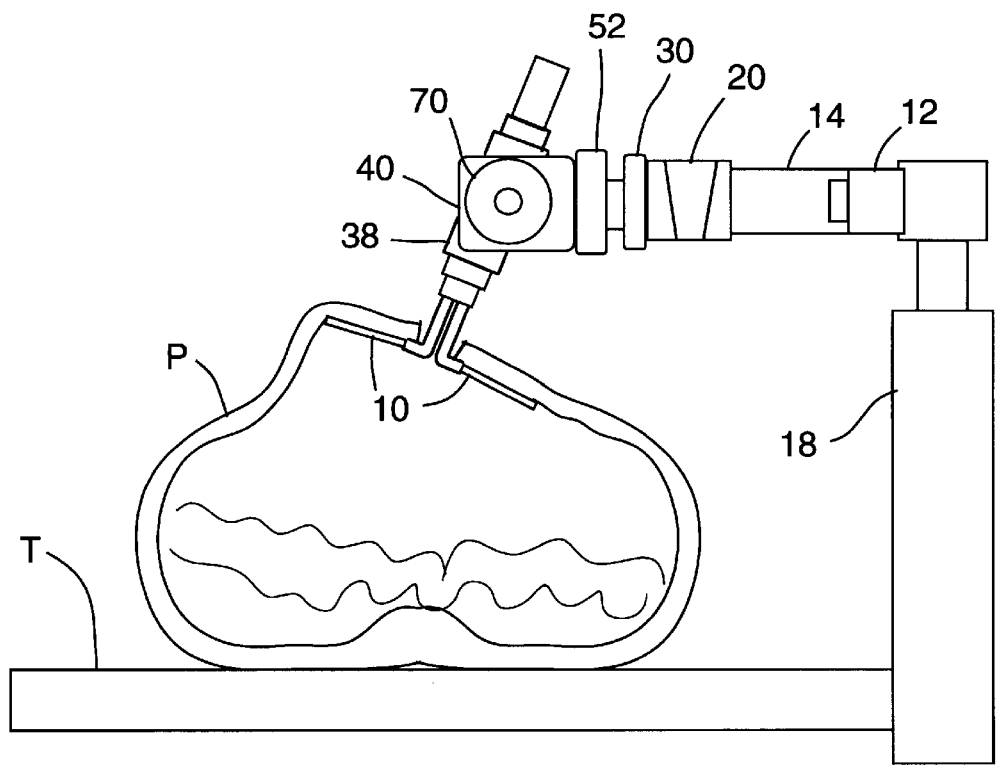
FIG. 8 is a cross-sectional elevational view corresponding to FIG. 7, showing the lifting device tilted as the result of roll adjustment with the connection of the present invention to provide additional space to one side of the patient's body.

Adjustment about the roll axis is also useful in a number of instances, for example:

a. If for any reason during surgery the operating table must be rotated, gravity will act on both the patient's body and the organs and shift their positions. Such a condition is shown in FIG. 5 where the table has been shifted. By adjusting the roll, the surgeon can return the lifting device to the desired angle, as shown in FIG. 6. The table could likewise be rotated to maneuver the patient into a laterally tilted position, or reverse laterally tilted position, and that could be compensated by pitch adjustment.

b. If for any reason during surgery the surgeon would like to change the amount or geometry of the exposure provided by the lifting device, he or she could adjust the roll, as shown in FIG. 8. FIG. 7 shows the internal exposure which would be provided by movement of the lifting device vertically, without roll adjustment. By adjusting roll as exemplified in FIG. 8, it is possible to lift more in the specific area of surgery.

c. In any circumstance where it is desired to make more room within a body cavity to one side or the other of the roll axis.

Pitch and roll adjustment with the embodiment of FIGS. 1, 2 and 9–12 is selectively effected by simply moving either the collar 52 or knob 70 to the position releasing the splines members associated therewith for rotation relative to one another and then moving the instrument to the desired position Once in the desired position, the sleeve 52 or knob 70 is released to reengage the splines, thus locking the instrument in the adjusted condition of pitch or roll.

Figure 13:
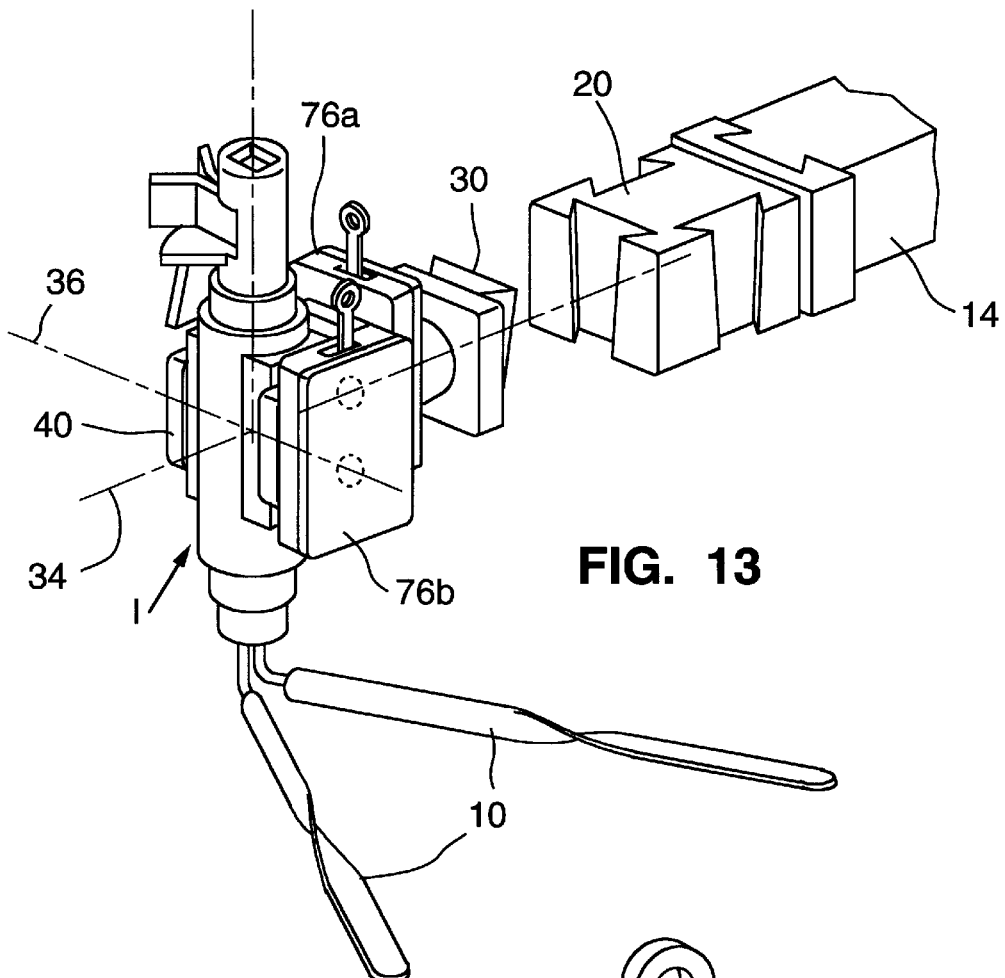
FIG. 13 is an exploded perspective view similar to FIG. 12, illustrating a second embodiment of the connector.
Figure 14:
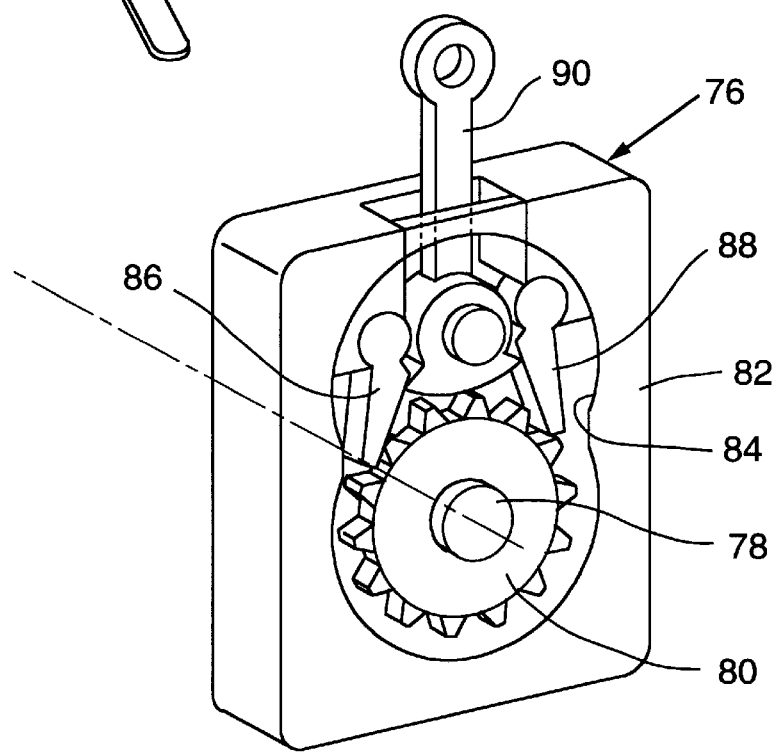
FIG. 14 is an enlarged perspective view of the ratchet used in the second embodiment connector, with the cover of the ratchet removed.

FIGS. 13 and 14 show a second embodiment wherein pitch and roll adjustment is achieved similarly to the aforedescribed adjustment, except that selective locking is provided by ratchet mechanisms. A shown in these Figures, elements corresponding to those of the previously described embodiments are designated by like numerals. The fork 40 is mounted for rotation about the pitch axis 34 and carries the instrument "I" for rotation about the roll axis 36. Rather than having the spline locking mechanisms, however, ratchet mechanisms 76 are provided, one for yaw adjustment and one for pitch adjustment. The ratchet mechanisms each comprise a shaft 78 rotatable about the axis therefore and having fixed thereto a ratchet wheel 80. The wheel 80 is mounted within a housing 82 having a chamber therein for receipt of the ratchet mechanism. The ratchet mechanism also includes pawls 86 and 88 pivotally mounted to the housing within the chamber 84 and an operating lever 90 supported between the pawls to selectively move one or the other of the pawls out of engagement with the ratchet wheel while the other is moved into engagement with the wheel.

As shown in FIG. 13, the ratchet mechanism for pitch adjustment is designated by the numeral 76a and the ratchet mechanism for roll adjustment is designated by the numeral 76b. These mechanisms correspond to the aforedescribed mechanism 76. The housing of the ratchet mechanism 76a is fixed to the bight portion of the fork structure 40. The shaft 78 of the mechanism 76a is fixed to the dovetail 30. The housing of the ratchet mechanism 76b is fixed to one leg of the fork structure 40 and the shaft 78 of this mechanism extends coaxially with the roll axis 36 for rotation within the leg of the structure 40 on which the mechanism is mounted. The distal end of the shaft 78 for the mechanism 76b is fixed to the housing 38 for the instrument "I," much in the same way that the sleeve 62 is fixed to the housing 38.

The FIG. 13 and 14 embodiment may be used in the same way as the embodiment of FIGS. 1, 2 and 9–12. As compared to the latter embodiment, however, the FIG. 13 and 14 embodiment has the advantage that the surgeon need only set the ratchet mechanisms with the operating levers therefor and then move the lifting instrument to the desired pitch and yaw angles. Upon release after such movement, the ratchet mechanism will automatically lock the instrument against return to the nonadjusted condition.

Figure 15:
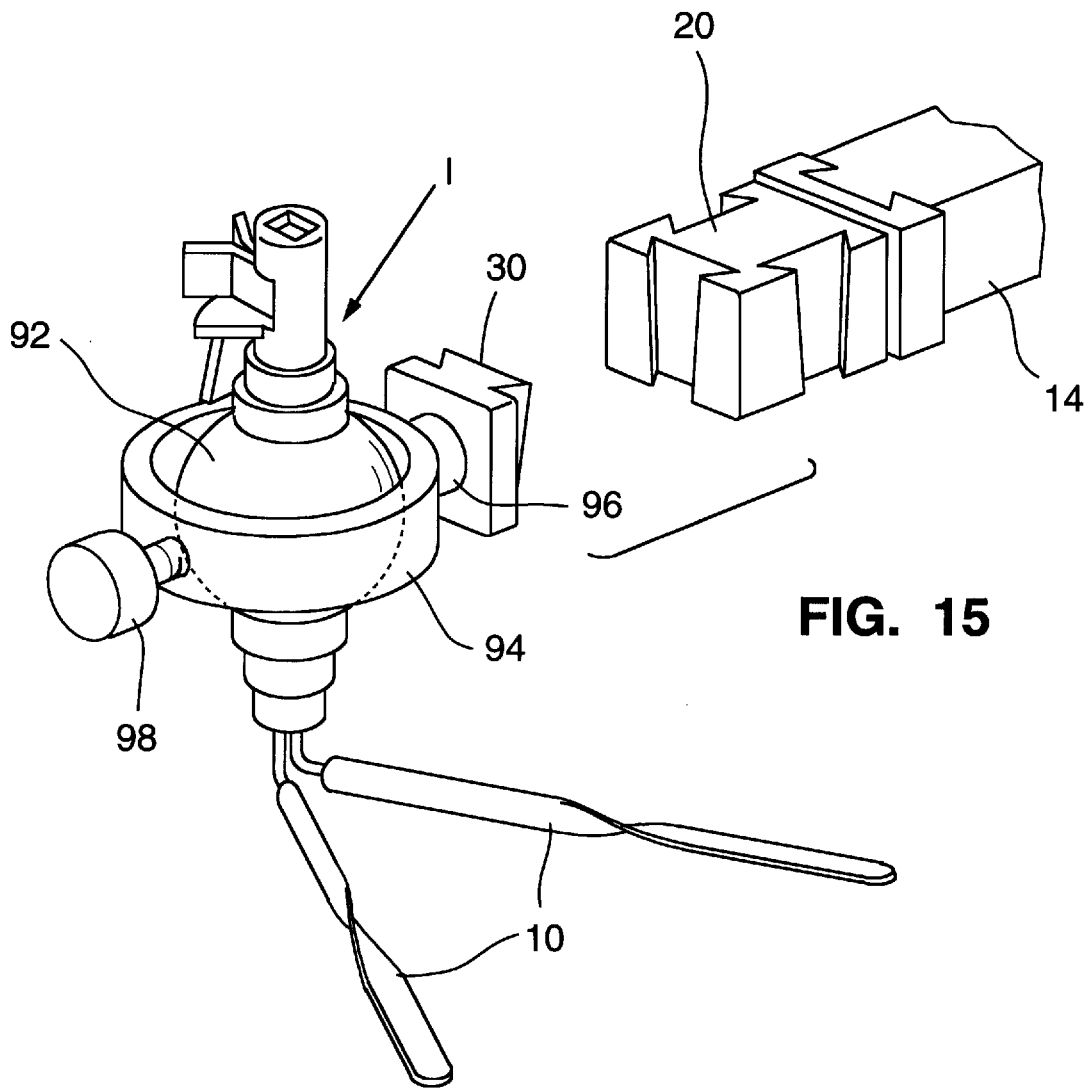
FIG. 15 is an exploded perspective view similar to FIGS. 2 and 13, illustrating a third embodiment connector.

FIG. 15 illustrates a simplified ball and socket mechanism for providing pitch and roll adjustment. Elements of this embodiment corresponding to those of the previous embodiments are designated by like numerals. In the FIG. 15 embodiment, the instrument "I" is mounted within a ball 92. Although the instrument may be mounted for free movement relative to the ball about the yaw axis, such movement is not necessary because the ball is free to rotate in all directions. The ball is rotatably received within a spherical collar 94 fixed to the dovetail 30 by a shaft 96. A set screw 98 extends threadably through the collar for select engagement with the ball 92 to lock the ball against rotational movement relative to the collar. If the ball is fixed relative to the instrument "I," this serves to lock against yaw, as well as pitch and roll. Although not illustrated, it should be understood that the interior end of the set screw 98 may be provided with a shoe to complementally engage the outside surface of the ball 92.

The FIG. 15 embodiment may be used in the same way as the aforedescribed embodiments. In the case of FIG. 15, it is simply necessary to release the set screw to provide for pitch and roll adjustment and then to tighten the screw when the desired adjusted condition is achieved.

CONCLUSION

While not described in detail with respect to each embodiment, it should be understood that the jack 18 may be selectively operated with all embodiments of the present invention to achieve desired lifting, or relaxation of lifting. To ease the pitch and roll adjustment, it is likely the surgeon would effect adjustment with the jack in a condition relaxing the arms 10 from significant lifting and then, once adjustment is achieved, activate the jack to elevate the wall of the body cavity being worked.

While specific embodiments of the invention have been illustrated and described, the invention is not intended to be limited to the specifics of these embodiments, but rather is defined by the accompanying claims.

We claim:

1. A method for selectively creating and altering the shape of a cavity within a patient's body by imparting internal forces to the body at select angles adjusted relative to horizontal, said method comprising:

a) inserting a lifting device having spaced lifting elements into the patient's body through a laparoscopic opening;

b) providing an elevationally adjustable lifting jack to the outside of the patient's body;

c) connecting the jack in load and torsion transmitting relationship to the lifting device through a joint having multiple axes adjustable relative to horizontal;

d) adjusting the rotational orientation of the lifting device relative to the jack and the resultant orientation of the lifting elements relative to horizontal by pivoting the lifting device about the axes of the joint;

e) locking the joint to fix the rotational orientation of the lifting device relative to the axes to dispose the lifting elements in a plane adjusted relative to horizontal; and f) adjusting the elevation of the lifting device through the lifting jack to impart lifting and torsional forces to the patient's body through the lifting elements and create a space within the body having an upper wall at a select inclination adjusted relative to horizontal.

2. A method according to claim 1 wherein the axes of the joint are horizontally disposed and extend at right angles relative to one another to provide, respectively, for pitch and roll adjustment of the lifting device relative to the jack.

3. A method according to claim 2 wherein the lifting device is connected to the jack for movement about a vertical axis for yaw adjustment of the lifting device relative to the jack.

4. A method according to claim 2 wherein the lifting device is connected to the jack for free unrestricted movement about a vertical axis during the application of lifting and torsional forces to the patient's body in response to elevation of the lifting device by the jack.

* * * * *

UNITED STATES PATENT AND TRADEMARK OFFICE
CERTIFICATE OF CORRECTION

PATENT NO. : 5,820,555

DATED : October 13, 1998

INVENTOR(S) : Watkins, III et al.

It is certified that error appears in the above-identified patent and that said Letters Patent is hereby corrected as shown below:

On the title page, Item [76] please delete inventors:
--Tim J. Kovac and Diane E. Caramore--.

Signed and Sealed this

Sixteenth Day of February, 1999

Attest:

Attesting Officer

Acting Commissioner of Patents and Trademarks